United States Patent
Darbut et al.

(10) Patent No.: US 11,194,071 B2
(45) Date of Patent: Dec. 7, 2021

(54) INTERCONNECT RING FOR MICROMINIATURE ELECTRICAL COIL

(71) Applicant: IntriCon Corporation, Arden Hills, MN (US)

(72) Inventors: Alexander L. Darbut, Edina, MN (US); Jeff Hoffmann, Bloomington, MN (US); William E. Tourdot, Arden Hills, MN (US); Taylor R. Stemler, Excelsior, MN (US); Sam A. Puent, Minneapolis, MN (US)

(73) Assignee: Intricon Corporation, Arden Hills, MN (US)

( * ) Notice: Subject to any disclaimer, the term of this patent is extended or adjusted under 35 U.S.C. 154(b) by 515 days.

(21) Appl. No.: 16/040,052

(22) Filed: Jul. 19, 2018

(65) Prior Publication Data

US 2019/0021630 A1    Jan. 24, 2019

Related U.S. Application Data

(60) Provisional application No. 62/534,607, filed on Jul. 19, 2017.

(51) Int. Cl.
| | |
|---|---|
| *G01V 3/10* | (2006.01) |
| *G01V 3/08* | (2006.01) |
| *A61B 5/06* | (2006.01) |
| *A61B 34/20* | (2016.01) |

(52) U.S. Cl.
CPC ............... *G01V 3/10* (2013.01); *A61B 5/062* (2013.01); *G01V 3/08* (2013.01); *A61B 2034/2051* (2016.02); *A61B 2562/0223* (2013.01)

(58) Field of Classification Search
CPC ......... A61B 5/062; A61B 5/064; A61B 34/20; G01V 3/104; G01V 3/081
See application file for complete search history.

(56) References Cited

U.S. PATENT DOCUMENTS

| | | | |
|---|---|---|---|
| 3,747,036 A * | 7/1973 | Erdmann | G08B 13/2497 336/84 R |
| 6,288,785 B1 | 9/2001 | Frantz et al. | |
| 6,385,482 B1 | 5/2002 | Boksberger et al. | |
| 6,553,326 B1 | 4/2003 | Kirsch et al. | |
| 6,625,465 B1 | 9/2003 | Moon et al. | |
| 6,836,745 B2 | 12/2004 | Seiler et al. | |
| 7,353,125 B2 | 4/2008 | Nieminen | |
| 7,469,187 B2 | 12/2008 | Nieminen et al. | |
| 7,783,441 B2 | 8/2010 | Nieminen et al. | |
| 7,957,925 B2 | 6/2011 | Nieminen et al. | |

(Continued)

*Primary Examiner* — Bo Joseph Peng
(74) *Attorney, Agent, or Firm* — Jeffrey D. Shewchuk; Shewchuk IP Services, LLC

(57) ABSTRACT

An interconnect ring is used in attaching the leadwires to the coil wire ends of a microminiature sensor. The interconnect ring is affixed directly to an outside surface of either the core or the coil wire of the microminiature sensor. At least the two flexible ends of the coil wire are electrically joined to metal pads on the interconnect ring. Thereafter, the microminiature sensor can be handled with minimal risk of breakage, shorting or dislodging of the ends of the coil wire. Two other metal pads on the interconnect ring are left open for subsequent attachment of leadwires which can run the length of the catheter device in which the microminiature sensor is used.

20 Claims, 7 Drawing Sheets

(56) References Cited

U.S. PATENT DOCUMENTS

| | | | |
|---|---|---|---|
| 2011/0089462 A1* | 4/2011 | Heerden | H01L 31/02002 257/99 |
| 2013/0066194 A1* | 3/2013 | Seter | A61B 5/062 600/424 |
| 2014/0012130 A1 | 1/2014 | Jacobsen et al. | |
| 2014/0061689 A1* | 3/2014 | Seibel | H01L 25/0753 257/89 |
| 2017/0358388 A1* | 12/2017 | Buesseler | G01B 7/003 |

\* cited by examiner

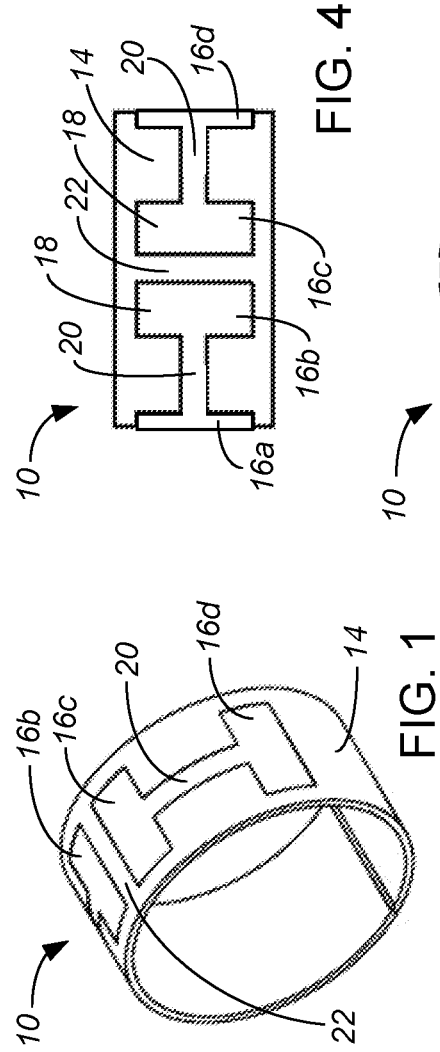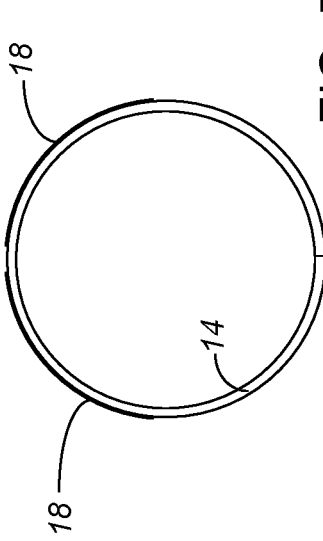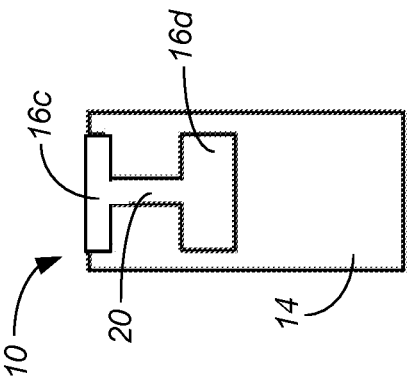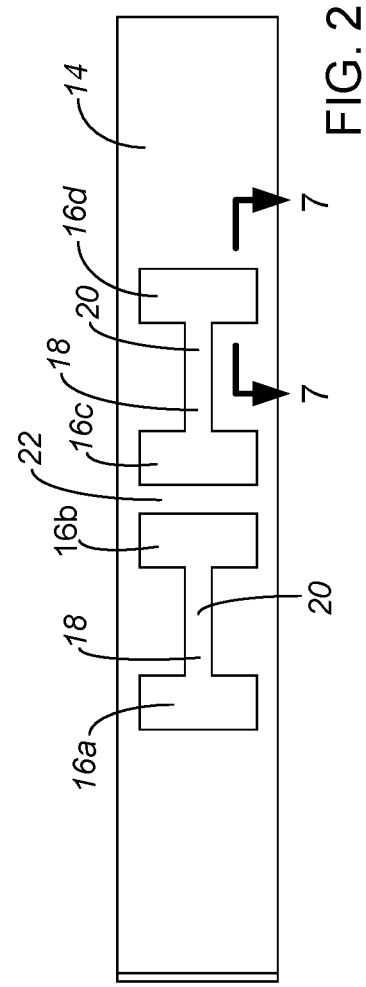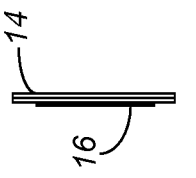

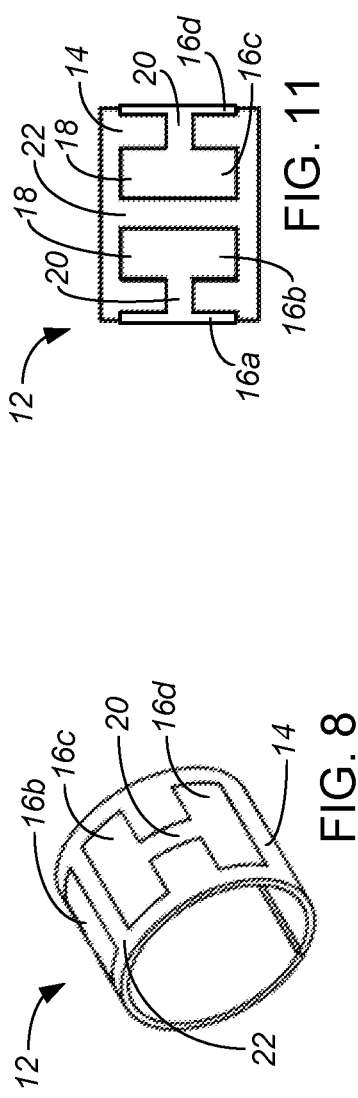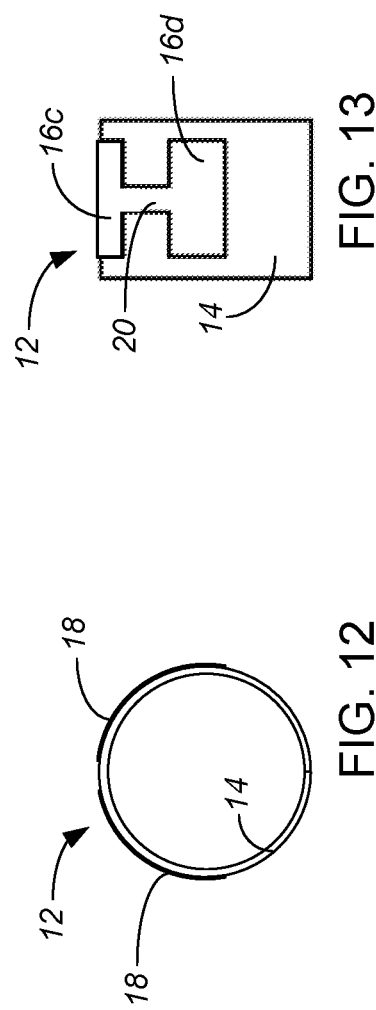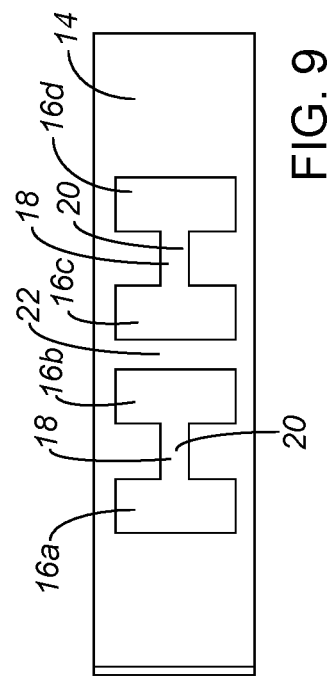

INTERCONNECT RING FOR MICROMINIATURE ELECTRICAL COIL

CROSS-REFERENCE TO RELATED APPLICATION(S)

The present application claims the benefit of U.S. provisional patent application Ser. No. 62/534,607, filed Jul. 19, 2017. The contents of U.S. provisional patent application Ser. No. 62/534,607 are hereby incorporated by reference in entirety.

BACKGROUND OF THE INVENTION

Microminiature electrical coils are used in various types of electronic and medical equipment, with an example being the AURORA electromagnetic tracking system provided by Northern Digital Inc. d/b/a NDI. Such electromagnetic tracking systems utilize a sensor coil to read electromagnetic fields, with a microprocessor based system interpreting the electrical response across the coil to determine a location of the coil in three-dimensional space. U.S. Pat. Nos. 6,288,785, 6,385,482, 6,553,326, 6,625,465, 6,836,745, 7,353,125, 7,469,187, 7,783,441 and 7,957,925 describe such systems, incorporated by reference.

A preferred prior art coil used in the electromagnetic tracking system uses an extremely thin copper wire (such as 58 AWG) wound around a core. The core may be a solid cylinder or a hollow tube or lumen. The core is typically formed of a ferrite-based or soft magnetic material, with a preferred core material being mu-metal. The core may be coated with a parylene layer to provide insulation.

An application of such systems is with the coil configured as part of a catheter, to electromagnetically track the location of the catheter coil within the human body during a medical procedure. For instance, example applications include the use of the sensor coil in an ablation catheter and the use of the sensor coil in a diagnostic catheter.

In the prior art manufacturing assembly process for creating the sensor coil, two wires are used as leads for the coil, with the two leadwires being twisted into a twisted pair. The leadwires are typically thicker than the coil wire, such as 40 AWG leadwires encased in insulation but with their ends stripped. The typical connection between the coil wire and the leadwires involves crudely wrapping the coil wire ends around each leadwire end and then soldering. Since the coil wire is very tiny, it is difficult to attach the larger 40 AWG lead wires to the smaller 58 AWG coil wire ends. The sensor coil is encapsulated, such as with a biocompatible UV adhesive over the top of the coil windings, termination points, and a minimum of three twists of sensor leadwires.

Problems have been identified with this prior art method of manufacture. A first problem which can occur is that one or both of the flexible ends of the coil wires may break. A second problem involves one or both leadwires, or one or both ends of the coil wire, pulling out of the adhesive encapsulation. A third problem can occur when a 3-point chuck on the mu-metal core bends the core out of a completely round circular tube. A fourth problem occurs if the adhesive bleeds or wicks into the inner diameter of the core. With adhesive residue in this location, further processing including assembly of the sensor coil onto the catheter can be difficult. A fifth problem in the prior art is a chance of shorting to the metal core if the assembly or soldering breaks through the parylene insulating layer on the core.

One proposed solution to such problems is disclosed in U.S. Pat. Pub. No. 20140012130, incorporated by reference, which discloses a flexible printed circuit sheet interposed between the lead wires and the ends of the coil wire. The flexible printed circuit sheet is positioned on the outer surface of a body of the catheter tube assembly. The flexible printed circuit sheet includes sets of two longitudinally spaced pads, with a proximal pad used for attachment of a leadwire, and a distal pad used for attachment of an end of a coil wire. While the structure of U.S. Pat. Pub. No. 20140012130 helps, many of the above-listed problems remain. In particular, the flexible ends of the coil wire which remain after winding the coil wire around the core are still subject to many potential breakage and shorting problems, especially while the coil is handled prior to complete assembly of the catheter. Further, the flexible printed circuit sheet requires real estate on the body of the catheter tube assembly, and generally requires fixation on the body of the catheter tube assembly prior to positioning and placement of the sensors and prior to attachment of the flexible ends of the coil wire to the pads. Better solutions are needed.

BRIEF SUMMARY OF THE INVENTION

The present invention involves an interconnection which assists in attaching the leadwires to the coil wire ends of a microminiature sensor, to avoid or minimize the problems of the prior art. Instead of being part of the catheter assembly or being affixed to a body in the catheter, the interconnection is affixed directly to an outside surface of either the core or the coil wire. At least the two flexible ends of the coil wire are electrically joined to pads on the interconnection. Thereafter, the microminiature sensor can be handled with minimal risk of breakage, shorting or dislodging of the ends of the coil wire.

BRIEF DESCRIPTION OF THE DRAWINGS

FIG. 1 is a perspective view of a first preferred embodiment of an interconnect ring in accordance with the present invention.

FIG. 2 is a plan view of the interconnect ring of FIG. 1 as formed in a flat state.

FIG. 3 is a side view of the interconnect ring of FIG. 2.

FIG. 4 is a top plan view of the interconnect ring of FIG. 1.

FIG. 5 is an end view of the interconnect ring of FIG. 1.

FIG. 6 is a side view of the interconnect ring of FIG. 1.

FIG. 8 is a perspective view of a second preferred embodiment of an interconnect ring in accordance with the present invention.

FIG. 9 is a plan view of the interconnect ring of FIG. 8 as formed in a flat state.

FIG. 10 is a side view of the interconnect ring of FIG. 9.

FIG. 11 is a top plan view of the interconnect ring of FIG. 8.

FIG. 12 is an end view of the interconnect ring of FIG. 8.

FIG. 13 is a side view of the interconnect ring of FIG. 8.

Figure 7:
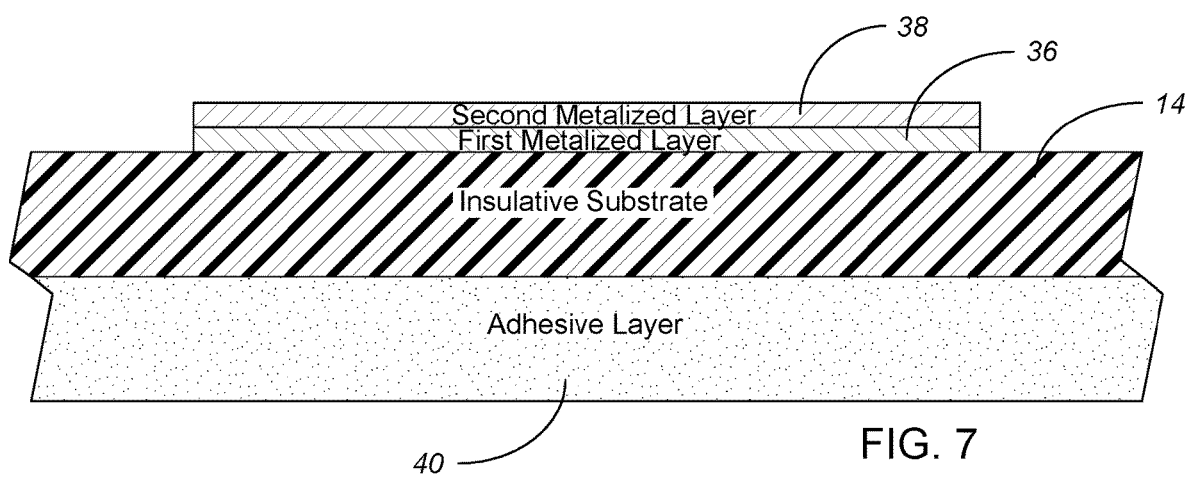
FIG. 7 is a cross-sectional view of the interconnect ring flat of FIGS. 2 and 3, taken along lines 7-7.

While the above-identified drawing figures set forth a preferred embodiment, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

Two preferred embodiments of an interconnect ring 10, 12 in accordance with the present invention are shown in FIGS. 1-13. The interconnect ring 10, 12 has a thin polymer based substrate 14. Four metallic electrode pads 16a, 16b, 16c, 16d are positioned on the substrate 14, preferably as two sets (16a and b, and 16c and d, respectively) of two interconnected pads each deposited as an H-shape 18 on the polymer ring 10, 12. Each pad is connected to one other pad via a small conductive path 20. The pads 16 need to be small enough that at least four pads 16a, 16b, 16c, 16d are present on the interconnect ring 10, 12, including adequate space 22 separating between the two sets (e.g., between pad 16b and pad 16c) so as to avoid potential shorting between the two sets of pads 16.

Figure 14:
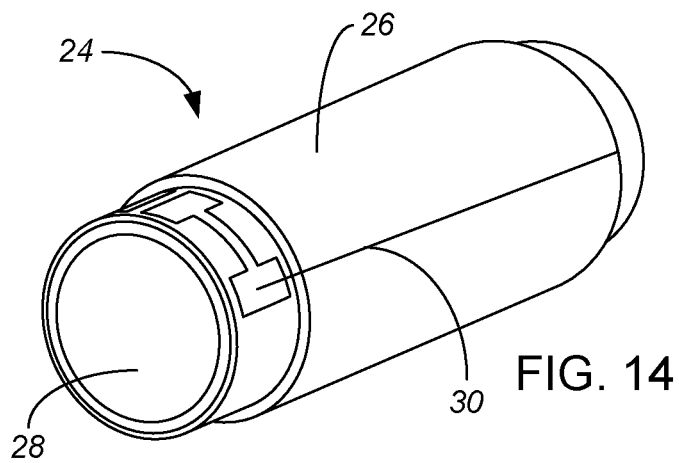
FIG. 14 is a first perspective view of the interconnect ring of FIGS. 1-7 attached onto the core of a sensor.
Figure 15:
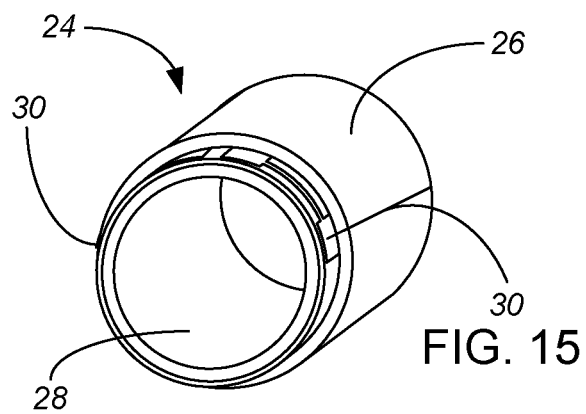
FIG. 15 is a second perspective view of the interconnect ring of FIGS. 1-7 attached onto the core of a sensor.
Figure 16:
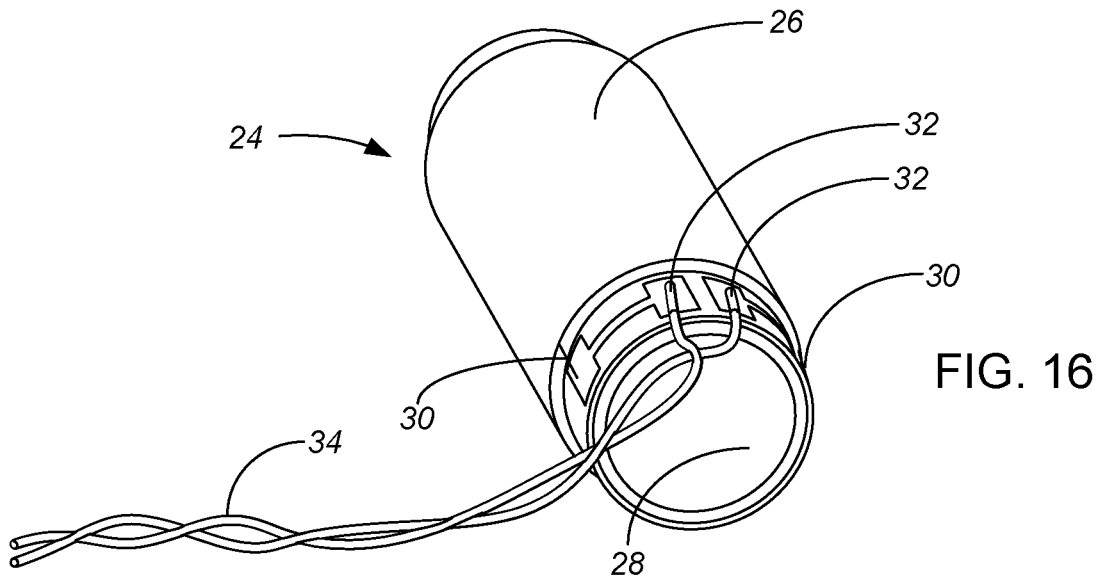
FIG. 16 is a third perspective view of the interconnect ring of FIGS. 1-7 attached onto the core of a sensor, and also showing a twisted pair connection wires attached to the pads of the interconnect ring.
Figure 17:
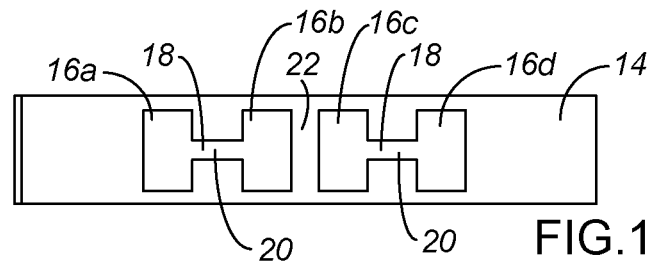
FIG. 17 is a plan view similar to FIG. 2.

The interconnect ring 10, 12 is used in a sensor 24 such as shown in FIGS. 14-16. In such sensors 24, a coil wire 26 is wound around a core 28, including a plurality of turns so as to be able to sense an electric, magnetic or electromagnetic field through body (human) tissue as is common in medical imaging. For instance, the coil wire 26 may be wound with about 100-1000 turns or more around the core 28, with an inductance in the microhenry-millihenry range. Alternative embodiments use the coil 26 for other purposes, such as for sensing temperature or pressure. The coil wire 26 is quite thin, typically having a size smaller than 40 AWG, such as within the range of 40-60 AWG. In the preferred examples shown in FIGS. 14-16, 24 and 25, the coil wire 26 is an insulated 58 AWG copper wire, meaning the copper wire is a tiny thread of about 0.0004 inches in diameter. For comparison, the thickness of a human hair is about 0.002-0.004 inches in diameter, i.e., about five to ten times thicker than the copper conductor of the coil wire 26. With the coil wire 26 being so very thin, the drawings of this patent application do not show the individual windings of the coil wire 26, but only show the flexible lead ends 30 of the coil wire 26. Being so very thin, the flexible coil wire 26 is also quite fragile.

The core 28 may be a solid cylinder or a hollow tube or lumen. The core 28 is typically formed of a magnetically permeable material such as a ferrite-based or soft magnetic material, with a preferred core material being mu-metal. The core 28 may be coated with a parylene layer (not separately shown) to provide insulation. Most cores 28 for such sensors 24 are cylindrical, but the core could alternatively have a more square, rectangular or other polygon or oval shape. In the most preferred embodiments, the core 28 is 0.197 inches in length and 0.057 inches in diameter.

The interconnect ring 10, 12 is small enough in area that it fits either on the outer surface of the coil windings 26, or on an exposed outer surface of the core 28. While the embodiments 10, 12 shown in FIGS. 1-13 extend 360° around the core 28, other embodiments extend at least 120° around the core 28 but less than 360°, such as in the range of 180 to 270° around the core 28. In essentially all embodiments, this will involve a diameter or width of 0.2 inches or less, used as a sensor 24 in medical imaging as part of a medical device such as a catheter. For example, the interconnect ring 10 of FIGS. 1-6 is cylindrical and has an inner diameter of 0.0371 inches, and a longitudinal dimension of 0.030 inches, while the interconnect ring 12 of FIGS. 8-13 is cylindrical with an inner diameter of 0.0566 inches, and a longitudinal dimension of 0.030 inches.

In the preferred embodiments of FIGS. 1-13, each pad 16 is rectangular, having a longitudinal dimension of 0.022 inches and a width of 0.010 inches. One of the pads 16a, 16d in each set is electrically connected to one of the flexible ends 30 of the coil wire 26. The other pad 16b, 16c in each set has sufficient open area to be electrically connected to a thicker wire, such as running the length of the catheter. For example, FIG. 16 shows the other pad 16b, 16c in each set electrically connected to a lead 32 of a twisted pair 34 of 40 AWG wires. The length of the twisted pair wires 34 depends upon the medical device in which the sensor 24 is used, but will typically be vastly longer than the sensor 24 itself, i.e., a typical length of 12 to 100 inches (only a short portion of the twisted pair 34 shown in FIG. 16).

The pads 16 are preferably circumferentially spaced on the substrate strip 14, at the same general longitudinal location. In the preferred embodiments, each of the four pads 16 is at the same longitudinal center line of the substrate strip 14, to be circumferentially spaced around the core 28. In the embodiments of FIGS. 1-13, the four pads 16 occupy positions at about 9 o'clock (16a), 11 o'clock (16b), 1 o'clock (16c) and 3 o'clock (16d) as depicted in FIGS. 5 and 12. When these preferred embodiments are used in a sensor 24 such as shown in FIGS. 14-16, the coil wire ends 30 are preferably connected to the outer two pads 16a, 16d (the 9 o'clock and 3 o-clock positions), while the inner two pads 16b, 16c (the 11 o'clock and 1 o-clock positions) are left exposed for the thicker connection wires 34. By leaving two adjacent pads 16b, 16c exposed, less of the twisted pair 34 needs to be untwisted and separated, and the two twisted pair wires 34 can be cut at the same length to attach into the two adjacent pads 16b, 16c at the same longitudinal position. In these preferred embodiments of FIGS. 1-13, the circumferential separation 22 between the two sets of pads 16 (i.e., the spacing between the 11 o'clock pad 16b and the 1 o'clock pad 16c is 0.005 inches. In the embodiment of FIGS. 1-7, the circumferential distance between the two pads 16 in each set (i.e., the length of the connection 20) is 0.021 inches. In the embodiment of FIGS. 8-13, the circumferential distance between the two pads 16 in each set (i.e., the length of the connection 20) is 0.010 inches.

The interconnect ring 10, 12 is preferably formed as part of a flat sheet structure. A cross-section of a preferred embodiment is shown in FIG. 7. The preferred base material is a heat formable polymer 14 which is electrically insulative, such as possibly a polyimide material, with a most preferred polymer being flat stock of LCP (Liquid Crystal Polymer) molded to be about 25 micron/0.001 inches thick. To form the electrically conductive portion of the electrode pads 16, a metal material is formed on the base material. The preferred method is to electro-plate or vacuum deposit two metalized layers: a first copper layer 36 at about 5 micron (0.0002 inches) thick, and then to add an electroless nickel immersion gold layer 38 at about 5 micron (0.0002 inches) thick. The two metalized layers 36, 38 are formed in the shape desired for the connection pads 16, such as the H-shape 18 shown. In one embodiment, an adhesive layer 40 is then added to the underside of the base material, with the preferred adhesive 40 layer being about 25 micron/1 mil thick.

In one embodiment, after this four-layer structure has been formed, it is heated and formed into a ring 10, 12. Alternatively, the multi-layer structure may be sufficiently flexible to curve into a ring 10, 12 without heat. When bent or curved into the ring 10, 12, the outer layer(s) of the multi-layer structure are forced to stretch to the larger outer diameter, while the inner layer(s) of the multi-layer structure are forced to compress to the smaller inner diameter. For example, a substrate strip 14 having a dimension of about 0.121 inches (FIG. 2) can be curved into a ring 10 having an inner diameter of about 0.037 inches (inner circumference of about 0.116 inches) and an outer diameter of about 0.042 (outer circumference of about 0.132 inches), and a longitudinal dimension of 0.030 inches, as shown in FIG. 1. A substrate strip 14 having a dimension of about 0.182 inches (FIG. 9) can be curved into a ring 12 having an inner diameter of about 0.057 inches (inner circumference of about 0.179 inches) and an outer diameter of about 0.062 (outer circumference of about 0.195 inches), and a longitudinal dimension of 0.030 inches, as shown in FIG. 8. The adhesive 40 can be applied only on the overlap structure of the ring 10, 12, adhering the polymer layer to itself, or alternatively can be applied over the entire underside of the polymer 14 as shown, not only adhering the polymer layer 14 to itself in a ring shape but also later adhering the ring 10, 12 to the core 28.

The inner diameter of the interconnection ring 10, 12 mates with the outer diameter of the core 28 such that assembly of the interconnection ring 10, 12 onto the core 28 is simple during mass production of such assemblies. In the 360° embodiments shown in FIGS. 1 and 8, one method of assembly is, after forming the ring 10, 12, advancing the ring 10, 12 longitudinally on the proximal end of the core 28, with the adhesive 40 layer holding the ring 10, 12 in position on the core 28. The four electrode pads 16 become locations for soldering, spot welding or laser attachment of the two leadwires 32 and the two ends 30 of the coil wire 26. The small conductive path connection 20 limits conductive heat transfer during attachment of the leadwires 32 and ends 30 of the coil wire 26.

While FIGS. 14-16 show the interconnect ring 10 attached to the core 28 at a region on the core 28 that is not covered with coil wire 26 but rather is longitudinally spaced from the core 28, note that the interconnect ring 10, 12 could alternatively be attached over the coil turns 26. Attaching the interconnect ring 10, 12 over the coil turns 26 allows for a sensor which is longitudinally shorter than the embodiment 24 of FIGS. 14-16. However, attaching the interconnect ring 10, 12 over the coil turns 26 increases the outer diameter of the sensor device 24. Additionally, attaching the interconnect ring 10, 12 over the coil turns 26 can affect the electrical or electromagnetic sensing characteristics of the sensor 24.

Figure 18:
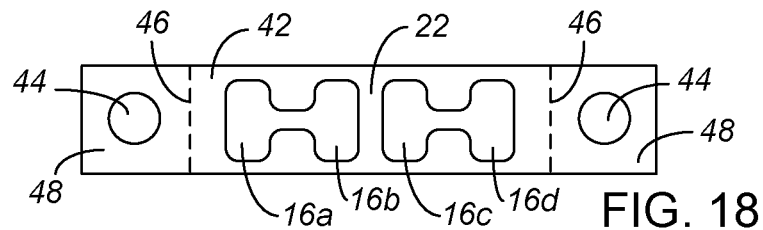
FIG. 18 is a plan view of a third preferred embodiment of an interconnect ring in accordance with the present invention.

FIG. 18 shows a third embodiment of an interconnect ring 42. In this embodiment, the ring 42 includes two through-holes 44. The through-holes 44 can be used for fixturing attachment, such as during deposition of the metal pad layers 36, 38 or during attachment of the interconnect ring 42 to the core 28 or coil 26. The embodiment of FIG. 18 also has a slightly different shape of pads 16, rounding the various corners of each pad. Rounding the corners of the pads 16 might minimize the possibility that the corners could catch, snag or flake off during manufacturing assembly of the catheter, or during deployment of the catheter/sensor inside a human body. The embodiment of FIG. 18 also has a separate distinction over the embodiments of FIGS. 1-17, namely the addition of tear or separation marks 46 which can be scored or otherwise added partially through the substrate 14 just outside of the pads 16. If desired, after the through-holes 44 are used in fixturing during metal deposition and/or attachment of the interconnect ring 42 to the core 28 or to the coil wire turns 26, the two ends 48 can be readily severed from the pad portion of the interconnect ring 42. The interconnect ring 42 then extends only part of the circumference of the core 28, reducing the size of the resultant sensor 24.

Figure 19:
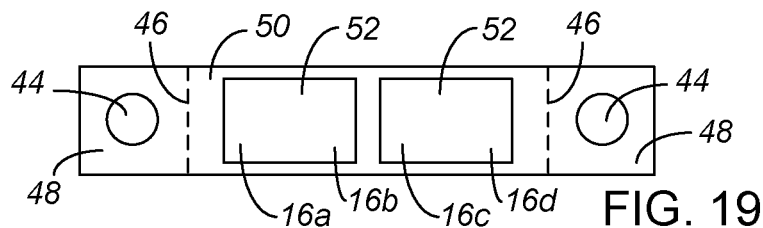
FIG. 19 is a plan view of a fourth preferred embodiment of an interconnect ring in accordance with the present invention.

FIG. 19 shows a fourth embodiment of an interconnect ring 50. In this embodiment, in addition to the separation marks 46, the shape of the pads 16 is changed. Rather than having an H-shape 18, the two pads 16 of each set are joined into a single rectangular shape 52. Another way of viewing the embodiment of FIG. 19 is that the length dimension of the connection 20 between each pad 16 in the two pad sets has been reduced to zero, so the two pads 16a, 16b abut and connect to each other and the two pads 16c, 16d abut and connect to each other. The interconnect ring 50 of FIG. 19 thus provides a larger open area to be electrically connected to twisted pair leads 32. However, heat applied during attachment of the twisted pair leads 32 can be conducted more directly to the ends 30 of the coil wire 26, making it more likely that attachment of the twisted pair leads 32 could soften, damage or degrade the electrical connection between the ends 30 of the coil wire 26 and their pad 16a, 16d.

Figure 20:
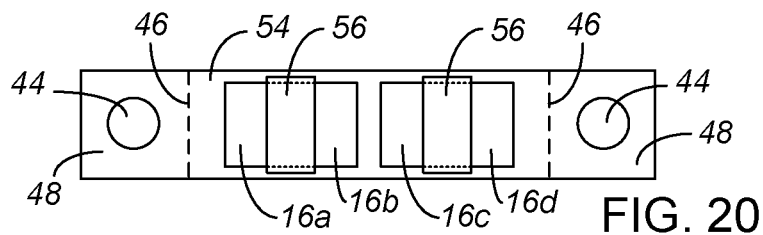
FIG. 20 is a plan view of a fifth preferred embodiment of an interconnect ring in accordance with the present invention.

The embodiment 54 of FIG. 20 is similar to the embodiment 50 of FIG. 19, but adds an additional insulative mask 56 in the center of each set of pads 16. The insulative mask 56 thus results in an interconnect ring 50 that performs much like the H-shaped interconnect ring 10, 12 of FIGS. 1-18, but making fabrication/deposition of the metal shape less detailed and sensitive.

Figure 21:
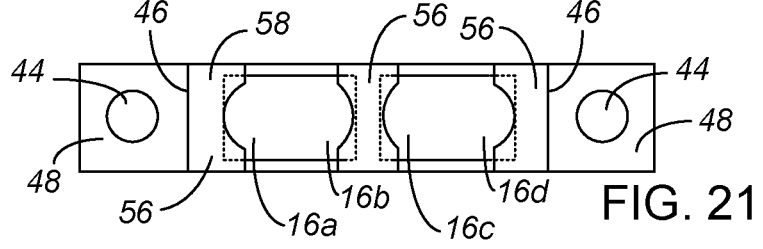
FIG. 21 is a plan view of a sixth preferred embodiment of an interconnect ring in accordance with the present invention.

The embodiment 58 of FIG. 21 is similar to the embodiment 54 of FIG. 20, but uses three insulative masks 56 rather than two. The three insulative masks 56 cover all the corners through an easier manufacturing process, without worrying about how sharp or rounded the corners of the pads 16 are as the metal layers are being deposited.

Figure 22:
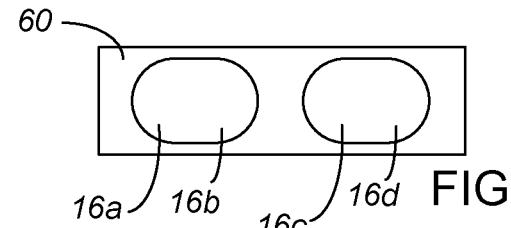
FIG. 22 is a plan view of a seventh preferred embodiment of an interconnect ring in accordance with the present invention.

The embodiment 60 of FIG. 22 is similar to the embodiment 58 of FIG. 21, but is formed directly by having the metal layer(s) deposited onto the polymer strip 14, and without any insulative masks 56. Additionally, no fixturing through-holes 44 are provided, but instead the strip 60 has a shorter dimension in the circumferential direction. When adhered to the core 28 or coil 26 of the diameters described above, this interconnect ring 60 only extends about 60% of the circumference. The term "ring" as used herein does not require a 360° wrapping of the circumference.

Figure 23:
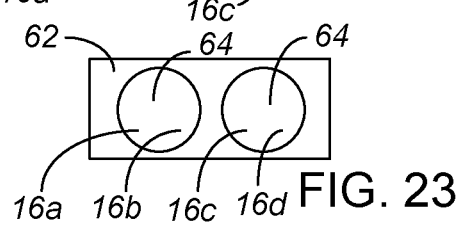
FIG. 23 is a plan view of an eighth preferred embodiment of an interconnect ring in accordance with the present invention.

The embodiment 62 of FIG. 23 is similar to the embodiment 60 of FIG. 22, but the pads 16 are laid down as two simple circles 64. One half of each circle is used as a pad 16a, 16d for the end 30 of the coil wire 26, while the other half of each circle is used as a pad 16b, 16c for the twisted pair leadwires 34.

Like the differences between each of the embodiments 10, 12, 42, 50, 54, 58, 60, 62 of FIGS. 17-23, workers skilled in the art will appreciated that various of these features can be combined, or other changes can be made, to achieve any specific set of goals and characteristics required of the interconnect ring.

Figure 24:
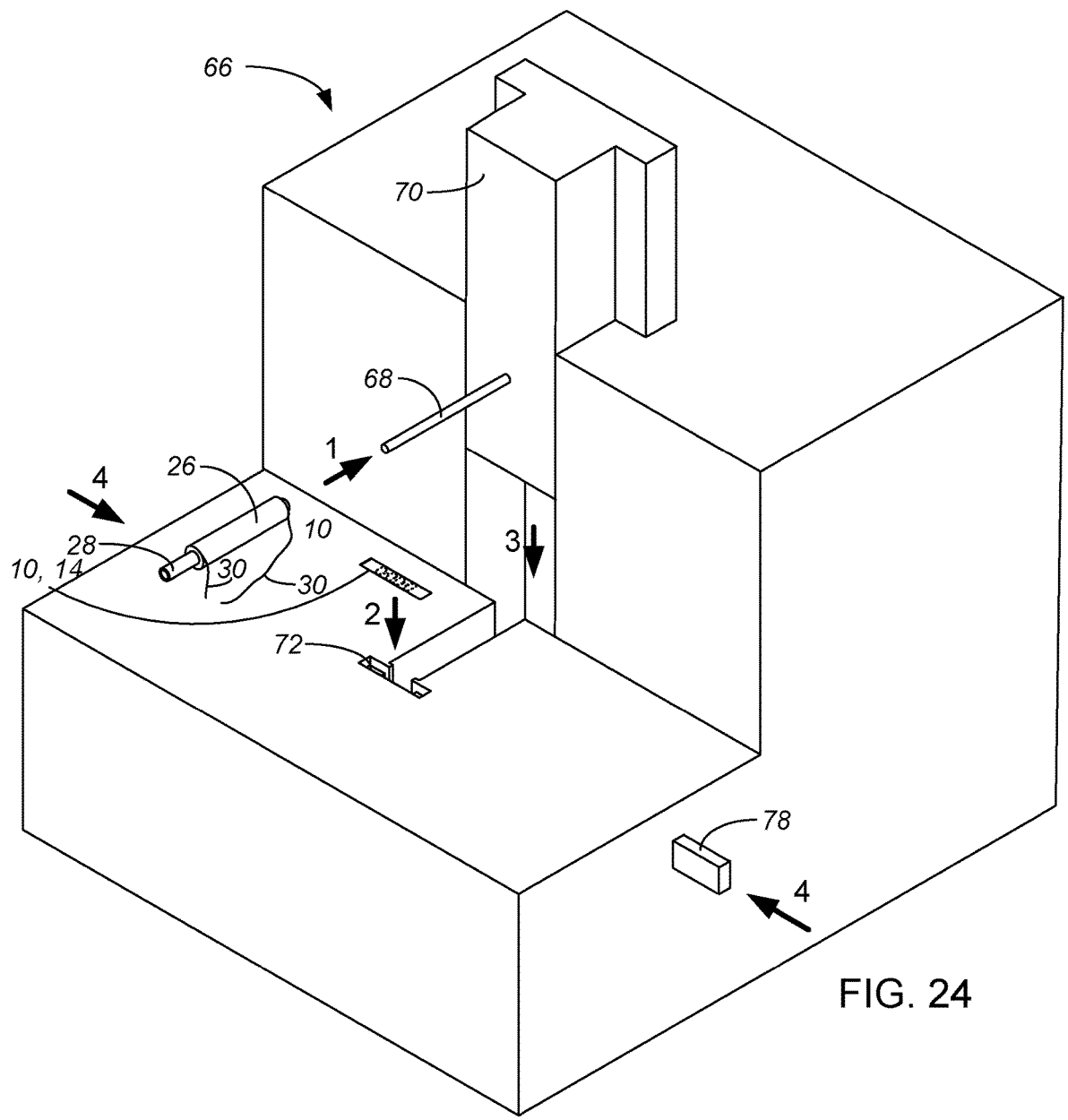
FIG. 24 is a perspective view of an assembly jig showing attachment of the interconnect ring of FIGS. 1-7 onto the core of the sensor.
Figure 25:
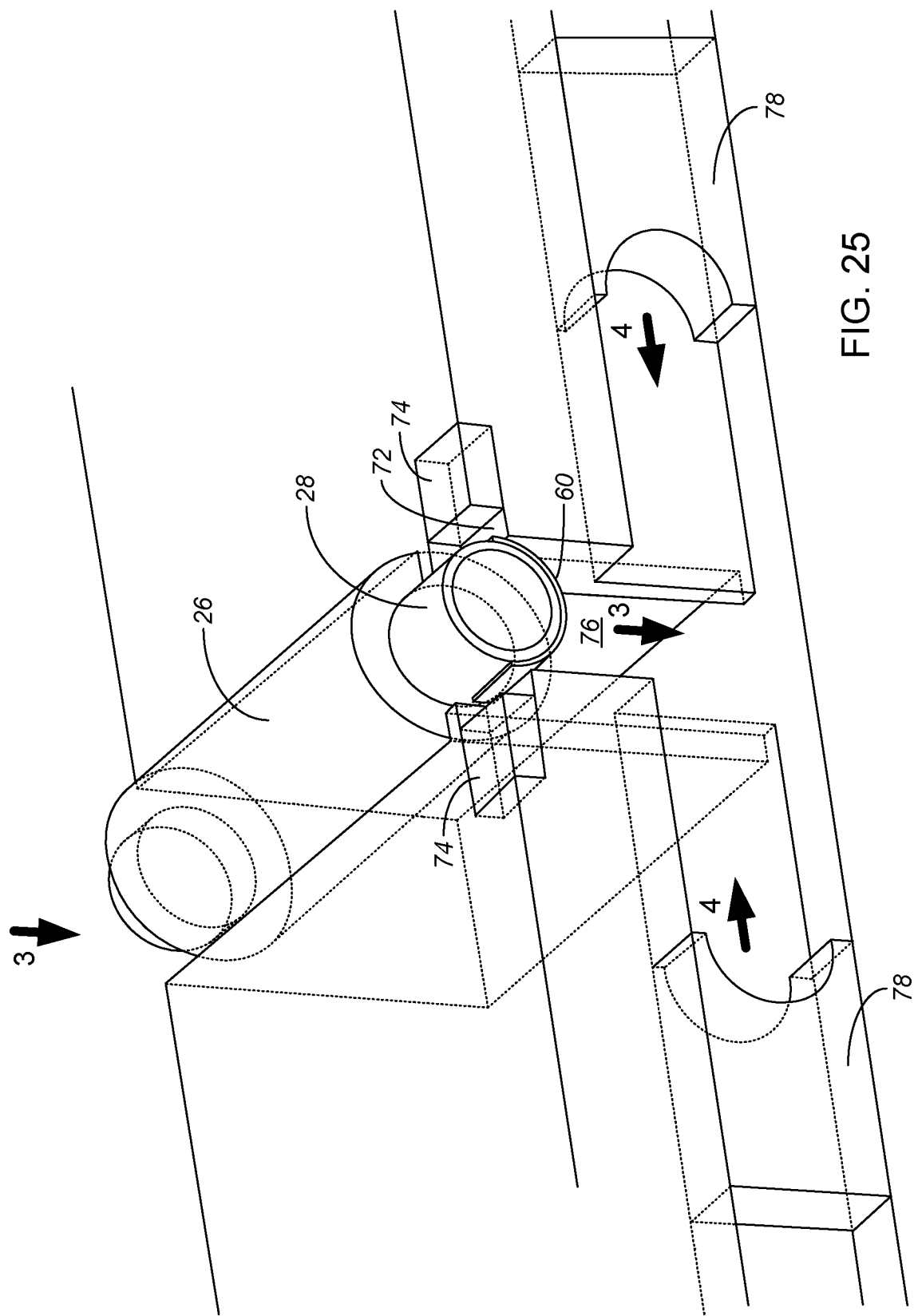
FIG. 25 is an enlarged perspective view of the assembly jig of FIG. 24, in cut-away and showing certain hidden lines, to explain the operation in attaching the interconnect ring of FIG. 22 onto the core of the sensor.

FIGS. 24 and 25 detail an assembly jig 66 that can be used in attaching any of the embodiments 10, 12, 42, 50, 54, 58, 60, 62 of FIGS. 17-23 to a sensor 24, without requiring pre-forming of the strip into a ring 10, 12. The assembly jig 66 includes a peg 68 on a vertically movable slide 70. The assembly jig 66 also includes a strip receiving recess 72. Depending upon the embodiment being assembled, inserts 74 (shown in FIG. 25) can adjust the size of the strip receiving recess 72 to match the size of the strip. The assembler places a sensor 24 over the peg 68 (labeled step 1), and places a strip 14, 60 in the strip receiving recess 72 (labeled step 2), perhaps using an appropriate tool such as a small tweezers (not shown). The strip 14, 60 is placed into the strip receiving recess 72 with its outer side facing downward. If an adhesive layer 40 was not included during formation of the strip 14, 60, the assembler may add the adhesive to the back side of the strip 14 at this time, such as using a syringe with a small needle (not shown) to deposit a small drop of adhesive. One preferred adhesive material is cyanoacrylate adhesive. After both the strip 14, 60 and the sensor 24 are in place and the adhesive applied, then the assembler slides the sensor 24 downward (labeled step 2) into contact with the adhesive on the strip 14, 60. The strip receiving recess 72 only supports the strip 14, 60 at its ends, leaving a center portion of the strip 14 extending over a further recess 76 for the core 28. The assembler further slides the sensor 24 downward, causing the flexible strip 14, 60 to curve or bend around the core 28 into the interconnect ring shape, while the bending of the flexible strip 14, 60 applies initial pressure to the adhesive. In all of the designs 10, 12, 42, 50, 54, 58, 60, 62 of FIGS. 17-23, the strip 14 is between 0.0005 and 0.002 inches thick depending on the manufacturer, and curving and flexing of the polymer strip 14 occurs without damage to the strip 14. After the slide 70 is fully lowered, two side slides 78 are pressed from the right and the left (labeled step 4) to complete the wrapping of the strip 14 around the core 28, and to complete the application of pressure onto the ring 10, 60 and against the core 28. Pressure can be maintained with the side slides 78 until the adhesive sets or cures, such as (depending upon the type of adhesive) using a UV, laser or heat curing process. If desired, movement of the slide 70 and side slides 78 may be mechanically linked, automated or otherwise coordinated.

After the adhesive is cured, the flexible ends 30 of the coil wire 26 are electrically connected to two of the pads 16a, 16d, such as through soldering, spot welding or laser attachment. By adhering the interconnect ring 10, 12, 42, 50, 54, 58, 60, 62 to the core 28 or to the coil wire 26, the length of the unwound fine gauge wire ends 30 is shortened due to the fact that the pads 16 are essentially located as close to the termination of the winding 26 as possible.

Note that at this point, the short flexible ends 30 of the coil wire 26 are secured in place and are much less likely to break or sever during further handling. The core 28 with the coil 26 and interconnect ring 10, 12, 42, 50, 54, 58, 60, 62 can be packaged as a microminiature electrical sensor unit 24, and more easily transported, delivered and handled prior to assembly into the catheter but after the ends 30 of the coil wire 26 have been electrically connected to their pads 16a, 16d. At a different location or time, the packaged microminiature electrical sensor unit 24 can be unpackaged and used in further manufacture of the catheter, including electrically connecting leads 32 of connection wires 34 running a length of the catheter.

The interconnection ring 10, 12, 42, 50, 54, 58, 60, 62 improves the quality of the electrical connection and the strength of mechanical connection for the wires 30, 32. The pull strength, particularly on the leadwires 34, is improved, resulting in fewer failures. With a better electrical connection, the electrical response of the coil wire 26 is more accurately transmitted to the lead wires 34 for reading with appropriate electrical equipment. Manufacturability is improved and made easier, and the resulting sensor is more reliable.

Although the present invention has been described with reference to preferred embodiments, workers skilled in the art will recognize that changes may be made in form and detail without departing from the spirit and scope of the invention. For instance, while only two sets of pads 16 are shown in the depicted embodiment, a third set of pads could be added to facilitating tapping at a middle location (not shown) of the coil 26.

What is claimed is:

1. A microminiature electrical sensor for use in a medical catheter,
comprising:
a core entirely formed of a magnetically permeable material and having a length, the core having a wrap outer surface extending circumferentially 360° around a longitudinal axis defined by the shape of the core;
a coil formed of a flexible, electrically insulated metal wire wrapped about the wrap outer surface of the core with a plurality of turns around the longitudinal axis for sensing through human tissue, the wrapping causing the wire to bend to the shape of the wrap outer surface, the coil having an outer diameter of no greater than 0.2 inches, the wire being smaller than 40 AWG (American Wire Gauge), the wire terminating in two lead ends extending flexibly from the turns;
an interconnect ring formed as a separate component to both the core and the coil, the interconnect ring being adhesively affixed to either the core or an outer surface of the coil, the interconnect ring comprising a polymer base substrate and at least two separate electrically conductive metal pads on the base substrate, with one of the lead ends of the coil electrically connected onto each pad, the interconnect ring having sufficient open area electrically connected to each of the at least two metal pads to electrically receive connection wires which are larger in thickness than the wire of the coil.

2. The microminiature electrical sensor of claim 1, wherein the core is cylindrical, and wherein the interconnect ring extends at least 120° around the longitudinal axis.

3. The microminiature electrical sensor of claim 1, wherein the core has an interconnect ring mounting surface longitudinally spaced from and adjacent the wrap outer surface.

4. The microminiature electrical sensor of claim 1, wherein each lead end of the coil wire is shorter than the length of the core.

5. The microminiature electrical sensor of claim 1, wherein the metal pads are formed with two layers of metal, with the two layers of metal jointly being thinner than the base substrate.

6. The microminiature electrical sensor of claim 5, wherein the two layers of metal comprise a lower layer of copper and an upper layer of electroless nickel immersion gold.

7. The microminiature electrical sensor of claim 1, wherein the wherein the substrate is less than 0.004 inches thick.

8. The microminiature electrical sensor of claim 1, wherein the substrate is formed of molded LCP (Liquid Crystal Polymer).

9. The microminiature electrical sensor of claim 1, wherein each metal pad comprises two rectangular connection areas connected into an H-shape by a connective path, with the connective path running transverse to the longitudinal axis such that the two rectangular connection areas are at the same longitudinal location but spaced circumferentially around the longitudinal axis, with one of the connection areas electrically connected to one lead of the coil, and with the other of the connection areas open for electrical connection to a connection wire.

10. The microminiature electrical sensor of claim 1, wherein the core is formed of a ferrite-based or soft magnetic material.

11. The microminiature electrical sensor of claim 1, wherein the core is formed of a solid cylinder of mu-metal.

12. The microminiature electrical sensor of claim 1, wherein the core is coated with a parylene layer to provide insulation under the coil.

13. The microminiature electrical sensor of claim 1, further comprising twisted pair connection wires, with an end of each of the connection wires in the twisted pair being electrically connected onto the open area of each pad.

14. The microminiature electrical sensor of claim 13, further comprising a biocompatible encapsulation over the core, the coil, the interconnect ring, and at least three twists of the twisted pair connection wires.

15. The microminiature electrical sensor of claim 13, disposed in a catheter, wherein the twisted pair connection wires run a length of the catheter.

16. The interconnect ring of claim 1, wherein the metal pads are formed with two layers of metal, with the two layers of metal jointly being thinner than the base substrate, wherein the two layers of metal comprise a lower layer of copper and an upper layer of electroless nickel immersion gold, and wherein the substrate is formed of molded LCP (Liquid Crystal Polymer).

17. A method of assembling a microminiature electrical sensor for use in a medical catheter, comprising:
   forming a core as a component formed entirely out of a magnetically permeable material, the core having a length and a wrap outer surface extending circumferentially 360° around a longitudinal axis defined by the shape of the core;
   wrapping a plurality of turns of flexible, electrically insulated metal wire about the wrap outer surface of the core to form a coil, the wrapping causing the wire to bend to the shape of the wrap outer surface, the wire being smaller than 40 AWG (American Wire Gauge), the coil having an outer diameter of no greater than 0.2 inches, the wire terminating in two lead ends extending flexibly from the turns, each lead end of the coil wire being shorter than the length of the core;
   forming an interconnect ring as a separate component to both the core and the coil, the interconnect ring comprising a polymer base substrate and at least two separate electrically conductive metal pads on the base substrate;
   adhesively affixing the interconnect ring to either the core or an outer surface of the coil; and
   electrically connecting the lead ends of the coil to the interconnect ring, one lead end onto each pad, the interconnect ring having sufficient open area electrically connected to each of the at least two metal pads to electrically receive connection wires which are larger in thickness than the wire of the coil.

18. The method of assembling of claim 17, wherein the adhesively affixing act comprises:
   forming the interconnect ring into a circular band, and
   inserting the coil with the wrapped coil thereon axially into the interconnect ring.

19. The method of assembling of claim 17, wherein the electrically connecting act comprises soldering, spot welding or laser attachment of the two lead ends of the coil wire to the pads of the interconnect ring.

20. The method of assembling of claim 17, further comprising:
   after the act of electrically connecting the lead ends of the coil to the interconnect ring, packaging the core with the coil and interconnect ring as a microminiature electrical sensor unit;
   transporting the packaged microminiature electrical sensor unit;
   unpackaging the microminiature electrical sensor unit; and
   inserting the unpackaged microminiature electrical sensor unit into a catheter, including electrically connecting leadwires of connection wires running a length of the catheter.

\* \* \* \* \*